(12) United States Patent
Alexanderson (10) Patent No.: US 7,585,252 B2
(45) Date of Patent: Sep. 8, 2009

(54) PERSONAL TRAINING DEVICE USING MULTI-DIMENSIONAL SPATIAL AUDIO

(75) Inventor: Ulf Petter Alexanderson, Lund (SE)

(73) Assignee: Sony Ericsson Mobile Communications AB, Nya Vattentornet (SE)

( * ) Notice: Subject to any disclaimer, the term of this patent is extended or adjusted under 35 U.S.C. 154(b) by 0 days.

(21) Appl. No.: 11/746,664

(22) Filed: May 10, 2007

(65) Prior Publication Data

US 2008/0280730 A1 Nov. 13, 2008

(51) Int. Cl.
*A63B 71/00* (2006.01)
(52) U.S. Cl. .............................................. 482/9; 482/3
(58) Field of Classification Search ..................... 482/3, 482/4, 7–9, 74, 900–901; 434/61, 255
See application file for complete search history.

(56) References Cited

U.S. PATENT DOCUMENTS

| | | | | |
|---|---|---|---|---|
| 5,240,417 | A * | 8/1993 | Smithson et al. | 434/61 |
| 5,371,799 | A * | 12/1994 | Lowe et al. | 381/310 |
| 5,809,149 | A | 9/1998 | Cashion et al. | |
| 5,976,083 | A * | 11/1999 | Richardson et al. | 600/300 |
| 6,013,007 | A * | 1/2000 | Root et al. | 482/8 |
| 6,152,856 | A * | 11/2000 | Studor et al. | 482/8 |
| 6,853,955 | B1 * | 2/2005 | Burrell et al. | 702/182 |
| 7,072,789 | B2 * | 7/2006 | Vock et al. | 702/141 |
| 7,085,678 | B1 * | 8/2006 | Burrell et al. | 702/182 |
| 7,220,220 | B2 * | 5/2007 | Stubbs et al. | 482/72 |
| 2002/0028730 | A1 * | 3/2002 | Kaufman | 482/8 |
| 2003/0139254 | A1 * | 7/2003 | Chang | 482/1 |
| 2003/0190896 | A1 * | 10/2003 | Ota et al. | 455/90.3 |
| 2005/0101439 | A1 * | 5/2005 | Berger | 482/8 |
| 2005/0107216 | A1 * | 5/2005 | Lee et al. | 482/8 |
| 2005/0197237 | A1 * | 9/2005 | Chen | 482/8 |
| 2005/0288154 | A1 * | 12/2005 | Lee et al. | 482/3 |
| 2006/0020177 | A1 * | 1/2006 | Seo et al. | 600/300 |

(Continued)

FOREIGN PATENT DOCUMENTS

WO 2004/058059 7/2004

(Continued)

OTHER PUBLICATIONS

International Search Report for corresponding Application No. PCT/IB2007/003360 dated Apr. 9, 2008.

*Primary Examiner*—Fenn C Mathew
*Assistant Examiner*—Andrew M Tecco
(74) *Attorney, Agent, or Firm*—Renner, Otto, Boisselle & Sklar, LLP (57) ABSTRACT

A personal training device is provided for a participant of pace-based physical training. The device includes an input for receiving an input signal indicative of a pace of the participant, and a comparator coupled to the input for comparing the pace of the participant to a predefined criteria. The personal training device further includes a training partner positioner for generating a position of a virtual training partner relative to the participant based on an output of the comparator, and a training partner audio source for providing audio representative of sounds from the virtual training partner. Still further, the personal training device includes a spatial audio processor for producing a multi-dimensional audio signal comprising the audio from the audio source, the multi-dimensional audio signal providing the audio at a spatial location represented by the position generated by the training partner positioner.

15 Claims, 4 Drawing Sheets

U.S. PATENT DOCUMENTS

| | | | |
|---|---|---|---|
| 2006/0040793 A1* | 2/2006 | Martens | 482/8 |
| 2006/0084551 A1* | 4/2006 | Volpe | 482/8 |
| 2006/0183603 A1* | 8/2006 | Astilean | 482/8 |
| 2007/0027000 A1* | 2/2007 | Shirai et al. | 482/8 |
| 2007/0042868 A1* | 2/2007 | Fisher et al. | 482/8 |
| 2007/0060446 A1* | 3/2007 | Asukai et al. | 482/8 |
| 2007/0149362 A1* | 6/2007 | Lee et al. | 482/8 |

FOREIGN PATENT DOCUMENTS

| | | |
|---|---|---|
| WO | 2007/017739 | 2/2007 |

* cited by examiner

FIG. 5 ized audio. Spatial audio presents a more realistic experi-
PERSONAL TRAINING DEVICE USING MULTI-DIMENSIONAL SPATIAL AUDIO

TECHNICAL FIELD OF THE INVENTION

The present invention relates generally to athletic training equipment, and more particularly to a personal training device based on spatialized audio.

Decription of the Related Art

Spatial audio is sound processed to give the listener the impression of a sound source within a multi-dimensional environment. Spatial audio presents a more realistic experience when listening to recorded sound compared to conventional stereo because stereo only varies across one axis, usually the x (horizontal) axis. Spatial audio may vary across two or more axes (e.g., x, y and/or z).

The principle of spatial audio is simple: if the sound waves arriving at a listener's eardrums are identical to those of a real audio source at a particular position, the listener will perceive that sound as coming from a source at that particular position. Because people only have two ears, only two channels of sound are needed to create this effect, and the spatial sound can be presented over ordinary two-channel headphones.

Many current spatial audio systems are based on digital filters derived from recordings made in the ear canals of live human subjects. (See, e.g., Wightman, F. L. & Kistler, D. J. (1989) Headphone simulation of free-field listening I: stimulus synthesis, J. Acoust. Soc. Am., 85, 858-867). True binaural spatial audio, when presented over headphones, appears to come from a particular point in the space outside of the listener's head. This is different from ordinary recorded stereo, which is generally restricted to a line between the ears when listened to with headphones.

The use of spatial audio has become increasingly prevalent in the computer gaming industry. Game players wear headsets that reproduce spatialized sound in order to simulate particular environments, etc. Such spatial audio tends to improve the overall gaming experience.

In the area of personal health and fitness, people typically devote many hours to physical training and conditioning. Such training frequently involves pace-based training such as jogging, running, cycling, rowing, swimming, etc. One of the problems associated with pace-based training is that oftentimes a person must train alone, without a partner. This can lead to training sessions that are less than fully effective.

For example, a runner training alone must push him or herself in order to maintain or improve his or her condition. When running in a group, a runner tends to at least "keep up" with the others. Each of the runners in the group relies on the others to push him or her to run faster, longer, etc. When running alone, a runner tends to lose track of his or her pace. This naturally leads to the runner failing to maintain or increase his or her pace. Consequently, a runner running alone is less likely to achieve an optimum workout. Moreover, a runner running alone is more likely to become bored and to lose interest in the session. Similar things can be said for participants of other types of pace-based training.

In view of the aforementioned shortcomings associated with training alone, there is a strong need in the art for a manner in which the training experience may be improved. In particular, there is a strong need in the art for a training device which can make training sessions more effective and more interesting by incorporating the above-discussed spatial audio techniques.

SUMMARY

According to an aspect of the invention, a personal training device is provided for a participant of pace-based physical training. The device includes an input for receiving an input signal indicative of a pace of the participant, and a comparator coupled to the input for comparing the pace of the participant to a predefined criteria. The personal training device further includes a training partner positioner for generating a position of a virtual training partner relative to the participant based on an output of the comparator, and a training partner audio source for providing audio representative of sounds from the virtual training partner. Still further, the personal training device includes a spatial audio processor for producing a multi-dimensional audio signal comprising the audio from the audio source, the multi-dimensional audio signal providing the audio at a spatial location represented by the position generated by the training partner positioner.

According to another aspect, the personal training device includes an accelerometer for providing the input signal.

In accordance with another aspect, the personal training device includes a global positioning system (GPS) receiver for providing the input signal.

In accordance with yet another aspect, the training partner positioner adjusts the position of the virtual training partner as a function of whether or not the partner is maintaining a predetermined pace.

According to another aspect, the predetermined pace is based on a training level preselected from among a plurality of different training levels.

In accordance with another aspect, the plurality of training levels each include a predetermined pace which varies as a function of time.

In yet another aspect, the predetermined pace is based on a preselected lap time or preselected pace.

According to still another aspect, the training partner positioner tends to advance the position of the virtual training partner relative to the participant when the runner fails to maintain the predetermined pace, and tends to decrease the position of the virtual training partner relative to the participant when the participant exceeds the predetermined pace.

In another aspect, the training partner positioner includes a pseudo-random component for varying the position of the virtual training partner.

According to another aspect, the audio provided by the training partner audio source includes the sound of footsteps of the virtual training partner.

In another aspect, the training partner audio source varies the frequency of the footsteps as a function of a change in position of the virtual training partner.

According to still another aspect, the training partner audio source varies the amplitude of the footsteps as a function of the position of the virtual training partner.

In still another aspect, the audio provided by the training partner audio source includes the sound of cycling.

In accordance with another aspect, the audio provided by the training partner audio source includes voice sounds of the virtual training partner.

According to another aspect, the personal training device is comprised within a portable electronic device.

In another aspect, the portable electronic device is a mobile phone.

In another aspect, the position of the virtual training partner is varied in at least two dimensions.

In still another aspect, multiple virtual training partners are provided simultaneously.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

It should be emphasized that the term "comprises/comprising" when used in this specification is taken to specify the presence of stated features, integers, steps or components but does not preclude the presence or addition of one or more other features, integers, steps, components or groups thereof.

DETAILED DESCRIPTION OF EMBODIMENTS

The present invention will now be described with reference to the drawings, in which like reference labels are used to refer to like elements throughout.

Figure 1:
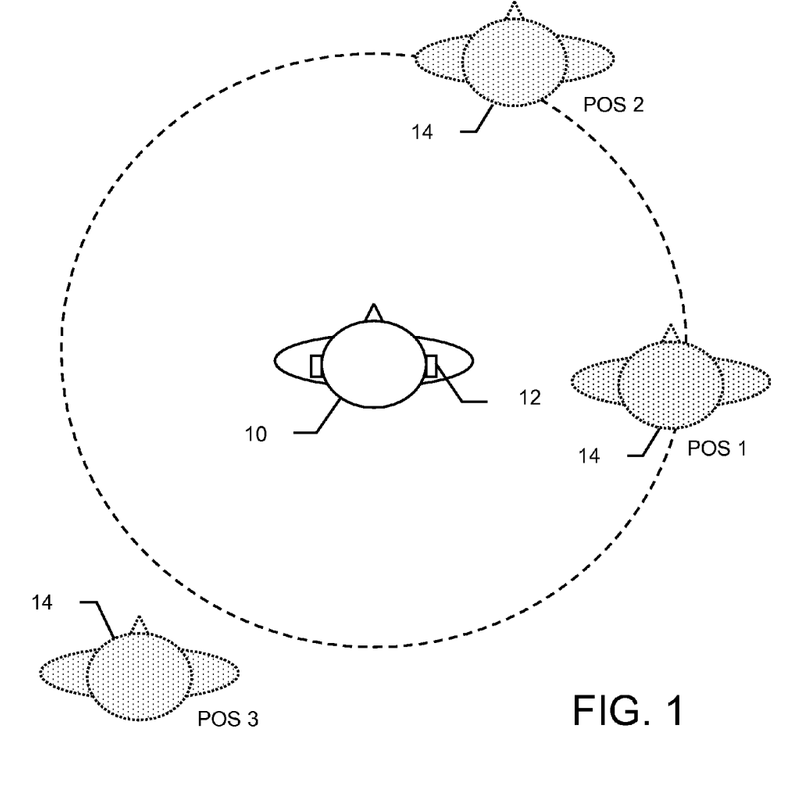
FIG. 1 represents a participant of pace-based training accompanied by a virtual training partner in accordance with an embodiment of the present invention.

Referring now to FIG. 1, a virtual environment is shown for a participant 10 of pace-based physical training utilizing a personal training device in accordance with the present invention. As will be explained in more detail below, the participant 10 wears a multi-channel (e.g., stereophonic) headset 12 suitable for reproducing a multi-channel audio signal. The audio signal is a multi-dimensional audio signal produced by a spatial audio processor capable of imaging a sound source reproduced by the headsets at two or more locations. The audio signal includes sounds of a virtual training partner 14. As in real-life, the spatial position of the virtual training partner 14 may vary based on the pace of the participant 10.

While the participant 10 engages in pace-based physical training such as walking, jogging, running, cycling, swimming, etc., the personal training device of the present invention monitors the pace of the participant 10 and compares the pace to a predefined pace criteria. Based on such comparison, the present invention produces the multi-dimensional audio signal such that the position of the virtual training partner 14 varies. Thus, for example, if the participant 10 tends to maintain a predefined pace, the present invention reproduces sounds representative of the virtual training partner 14 via the headset 12 such that the virtual training partner 14 appears audibly to be positioned adjacent the participant 10 (e.g., at POS1 to the right of the participant 10).

Should the participant 10 fall behind a predefined pace, the invention reproduces the sounds of the virtual training partner 14 such that the virtual training partner 14 appears audibly to advance in position relative to the participant 10 (e.g., by transitioning in position from POS1 to POS2 located ahead of the participant 10). Similarly, should the participant 10 exceed a predefined pace, the invention reproduces the sounds of the virtual training partner 14 via the headset 12 such that the virtual training partner 14 appears audibly to fall back in position relative to the participant 10 (e.g., by transitioning in position from POS2 to POS3 located behind the participant 10).

The multi-dimensional sounds reproduced by the personal training device of the present invention preferably include sounds indicative of the type of pace-based training in which the participant 10 is engaged. For example, if the participant 10 is engaged in walking, jogging or running, the sounds may include footsteps indicative of the footsteps of the virtual training partner 14. The present invention may vary the amplitude of the footsteps based on the relative distance between the participant and the virtual training partner 14 at any given time. Moreover, the present invention may vary the frequency of the footsteps depending on whether the virtual training partner 14 is increasing or decreasing his or her pace at any given time.

In the case of another form of pace-based training, such as cycling, the sounds reproduced by the personal training device may include the cycling sounds of the virtual training partner 10 (e.g., sounds of the chain moving along the sprockets, wheel noise, etc.).

Still further, the multi-dimensional sounds reproduced by the personal training device of the present invention may include physiological sounds of the virtual training partner 14. For example, such physiological sounds may include the sound of heaving breathing coming from the virtual training partner 14. In addition, or in the alternative, the sounds may include voice sounds coming from the virtual training partner 14. As an example, the voice sounds may include encouragement such as "Keep it up", "Come on, you can do it", "Let's go, stay with me", etc. As another example, such voice sounds may include proverbial "trash talk", such as "What's wrong, can't keep up with me?", "You think you are good?", "My two-year old can go faster than you", etc.

As will be appreciated, various types of sounds will be appropriate for the virtual training partner 14 based on the particular type of pace-based training being engaged. The present invention contemplates any and all such sounds.

Accordingly, the personal training device of the present invention makes training sessions more effective and more interesting by incorporating the above-discussed spatial audio techniques. The sounds and positioning of the virtual training partner 14 relative to the participant 10 serve to motivate the participant 10 to maintain and/or improve his or her pace within the pace-based training.

Figure 2:
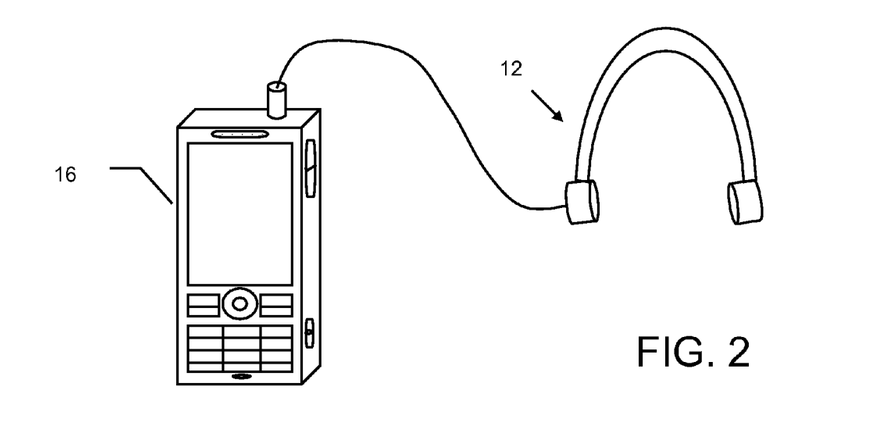
FIG. 2 is a perspective view of a mobile phone incorporating a personal training device in accordance with an embodiment of the present invention.

FIG. 2 illustrates a mobile phone 16 incorporating the personal training device of the present invention. The mobile phone 16 can be conveniently carried by the participant 10 during the particular pace-based physical training and perform the functions described herein as well as conventional mobile phone functions. It will be appreciated, however, that the personal training device of the present invention may be a dedicated device or part of another type of electronic device such as a personal digital assistant (PDA), pager, etc., without departing from the scope of the invention.

Figure 3:
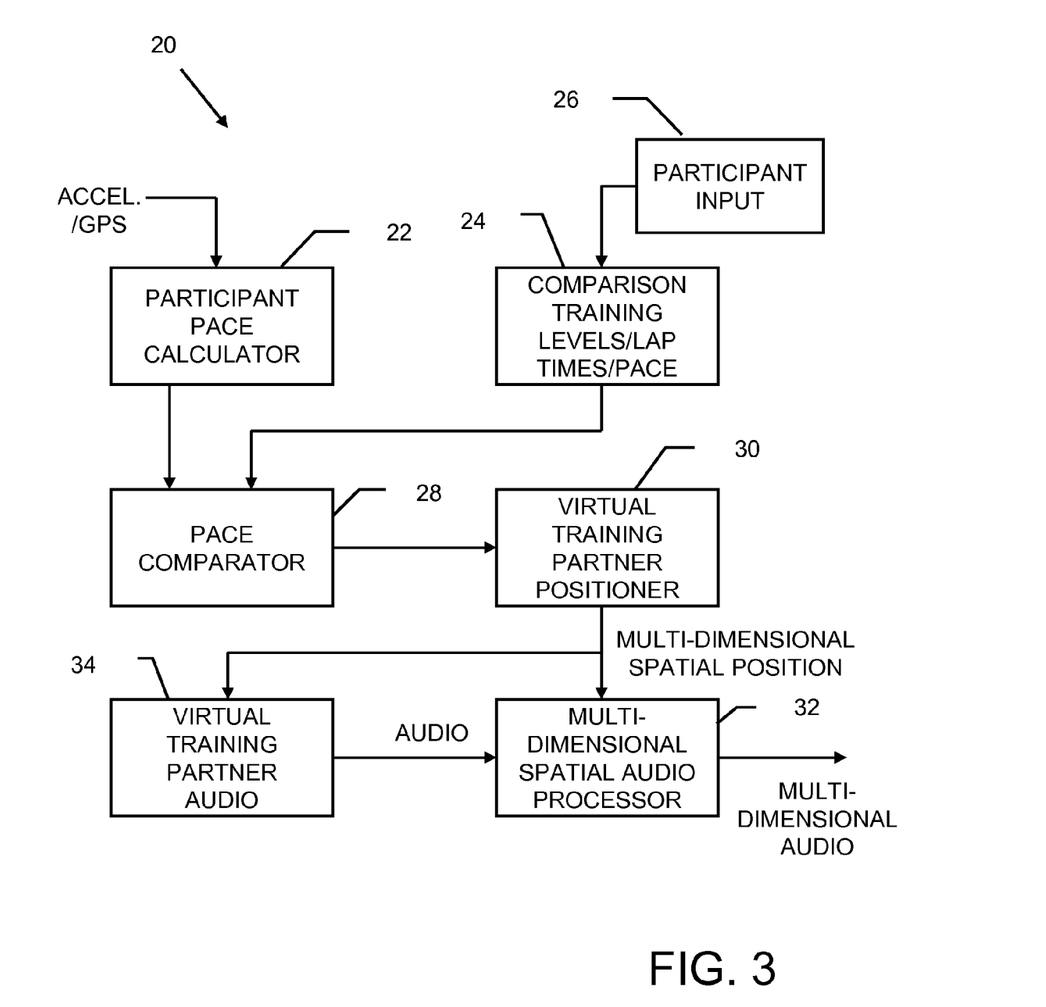
FIG. 3 is a block diagram of a personal training device in accordance with an embodiment of the present invention.

FIG. 3 is a block diagram of a personal training device 20 in accordance with an exemplary embodiment of the present invention. The personal training device 20 includes a participant pace calculator 22 which receives, as an input, a signal indicative of the pace of the participant 10 during pace-based physical training. In accordance with the present invention, the input signal can be any type of signal indicative of the pace of the participant. For example, an accelerometer (not shown) may be used to provide the input signal to the participant pace calculator 22 in the case of pace-based physical training involving motion of the participant 10 (e.g., walking, running, jogging, biking, rowing, etc.). Alternatively, for example, a pedometer worn by the participant 10 may provide the input signal to the participant pace calculator 22. The participant pace calculator 22 processes the output of the accelerometer or pedometer using well-known techniques in order to determine the speed or pace of the participant 10.

According to another embodiment, a global positioning system (GPS) receiver (not shown) may be used to provide the input signal in place of the accelerometer, pedometer, etc. The GPS receiver provides information on the position of the participant 10. The participant pace calculator 22 processes the output of the GPS receiver, again using well-known techniques, in order to determine the speed or pace of the participant 10. In still another embodiment, the input signal may be based on a different type of sensor. For example, the speedometer of a bicycle used by the participant 10 during biking may provide the input signal. As yet another alternative, the output of a sensor that senses the number of revolutions of the pedal on a stationary bike, the output of a sensor that senses the rowing frequency of a stationary rowing machine, etc., may serve as the input to the participant pace calculator 22. Still further, techniques such as triangulation (e.g., via GSM) may be utilized to track the position, and hence the speed or pace of the participant 10. The participant pace calculator 22 is configured to perform conventional processing of the input signal in order to ascertain the pace of the participant 10. In turn, the participant pace calculator 22 outputs a signal representing the pace of the participant 10.

The personal training device 20 also includes a comparison data block 24 that includes data indicative of a predefined pace criteria to which the pace of the participant 10 is to be compared. The comparison data block 24 may include predefined pace criteria in accordance with any of a variety of embodiments. For example, the comparison data block 24 may include pace data corresponding to a plurality of different training levels. A beginner level may include pace data reflecting a moderate pace. An intermediate training level may include pace data indicative of a medium level pace, and an expert training level may include pace data reflecting an expert pace. Still further, some training levels may be designed such that the virtual training partner 14 proceeds at a pace generally behind the participant 10 so as to "push" the participant 10 from behind. Moreover, some training levels may be designed such that the virtual training partner 14 proceeds at a pace generally ahead of the participant 10 so as to "pull" the participant 10. The number of training levels can be any number as will be appreciated.

Furthermore, the pace data for the different training levels may include different profiles that reflect variations in pace over time. As will be appreciated, such variations tend to guide the participant 10 through a workout that increases and/or decreases in pace along the predefined profile. For example, a given profile may represent a triangular waveform which ramps up in pace and then drops down and gradually ramps up again.

According to another embodiment, the predefined pace criteria may represent target lap times for the participant 10. For example, a participant 10 training at a track for a 10K running marathon may input a desired lap time in order to complete the 10K within a desired amount of time. The comparison data block 24 can, in turn, convert the desired lap time into corresponding pace data necessary to complete the lap(s) within the desired time. As yet another alternative, the participant 10 may simply directly input a desired pace (e.g., meters per minute, etc.). The personal training device 20 includes a participant input device 26 such as a keypad, touch screen, etc., that permits the participant 10 to select/enter the desired training levels, lap times, etc.

The personal training device 20 further includes a pace comparator 28 which receives the output of the participant pace calculator 22 representing the pace of the participant 10. Also input to the pace comparator 28 is the selected/entered comparison data output from the comparison data block 24. The output of the comparison data block 24 is indicative of the predefined pace criteria to which the pace of the participant 10 is to be compared based on the selected training levels, lap times, etc., as described above.

The pace comparator 28 compares the pace of the participant 10 to the predefined pace criteria, and based on such comparison outputs a signal indicative of whether the participant 10 is currently maintaining, exceeding, or lagging the pace represented by the predefined pace criteria. The output of the pace comparator 28 is provided to a virtual training partner positioner 30 also included in the personal training device 20.

As is exemplified in FIG. 4 discussed below, the virtual training partner positioner 30 generates a position of the virtual training partner 14 relative to the participant 10 based on the output of the pace comparator 28. Generally speaking, the virtual training partner positioner 30 preferably causes the position of the virtual training partner 14 relative to the participant 10 to be maintained provided the output of the pace comparator 28 indicates that the participant 10 is maintaining the pace represented by the output of the comparison data block 24. The virtual training partner positioner 30 preferably causes the position of the virtual training partner 14 relative to the participant 10 to advance provided the output of the pace comparator 28 indicates that the participant 10 is falling behind the pace represented by the output of the comparison data block 24. Finally, the virtual training partner positioner 30 preferably causes the position of the virtual training partner 14 to decrease relative to the participant 10 provided the output of the pace comparator 28 indicates that the participant 10 is exceeding the pace represented by the output of the comparison data block 24.

According to the above-described operation of the virtual training party positioner 30, it will be appreciated that the position of the virtual training partner 14 relative to the participant 10 primarily varies in the fore/aft directions relative to the movement of the participant 10. However, it will be appreciated that the position of the virtual training partner 14 may also be moved laterally (e.g., left/right) relative to the position of the participant 10. The virtual training partner positioner 30 may be configured to introduce such lateral movement of the position of the virtual training partner 14 somewhat randomly (i.e., independent of the relative position of the participant 10). In addition, or alternatively, the virtual training party positioner 30 may be configured to provide lateral movement of the position of the virtual training partner 14 in relation to lateral movement of the participant 10. As will be appreciated, the output of a multi-axis accelerometer the GPS receiver, triangulation receiver, etc., as provided as an input to the participant pace calculator 22 will also be indicative of lateral movement of the participant 10 during the training session. Such indication of lateral movement can be input to the virtual training partner positioner 30 in order to generate corresponding lateral position of the virtual training partner 14 relative to the lateral change in position of the participant 10.

In yet another embodiment, the virtual training partner positioner 30 may also generate a position of the virtual training partner 14 along a third axis (e.g., vertical axis). Depending on the particular pace-based training involved, movement of the virtual training partner 14 along a third axis may be desirable.

The virtual training partner positioner 30 provides as an output current location information of the virtual training partner 14 relative to the participant 10, such current location being determined as described herein. Such location information is in turn provided to a multi-dimensional audio processor 32 also included in the personal training device 20. In addition, the multi-dimensional audio processor 32 receives virtual training partner audio sounds from a virtual training partner audio source 34 also included in the personal training device 20. Using known multi-dimensional audio processing techniques, the multi-dimensional audio processor 32 processes the virtual training partner audio sounds so as to produce a multi-dimensional audio signal providing the virtual training partner audio at a spatial location represented by the position generated by the virtual training partner positioner 30. The multi-dimensional audio processor 32 outputs the multi-dimensional audio signal so that the multi-dimensional audio signal may be reproduced via the headset 12 or other audio reproduction means. Thus, when the participant 10 listens to the multi-dimensional audio signal reproduced by the headset 12 during training, the position of the virtual training partner 14 within the audio field will vary in accordance with variations in the position generated by the virtual training partner positioner 30.

The virtual training partner audio source 34 has audio sounds stored therein representative of the virtual training partner 14. As explained above, if the participant 10 is engaged in walking, jogging or running type training, the sounds stored in the virtual training partner audio source 34 may include footsteps indicative of the footsteps of the virtual training partner 14. In the case of another form of pace-based training, such as cycling, the sounds stored in the virtual training partner audio source 34 may include the cycling sounds of the virtual training partner 10 (e.g., sounds of the chain moving along the sprocket, wheel noise, etc.). Still further, the sounds stored in the virtual training partner audio source 34 may include physiological sounds of the virtual training partner 14 such as heaving breathing. In addition, or in the alternative, the sounds may include voice sounds from the virtual training partner 14.

The corresponding sounds associated with the virtual training partner audio source 34 may be prerecorded and stored in memory. For example, the personal training device 20 may include a memory having stored therein common sounds associated with various types of training. In addition, or in the alternative, the participant 10 can use the personal training device 20 to download and store selected sounds associated with desired types of training.

The virtual training partner audio source 34 may receive, as an input, the spatial position of the virtual training partner 14 relative to the participant as output by the virtual training partner positioner 30. The virtual training partner audio source 34 may in turn be configured to monitor a change in such relative position. For example, the virtual training partner audio source 34 may be configured to vary the amplitude of the sound of footsteps based on a change in the relative distance between the participant and the virtual training partner 14 at any given time. If the virtual training partner 14 and the participant 10 move closer in distance to each other, the virtual training partner audio source 34 may increase the amplitude of the footsteps provided to the multi-dimensional audio processor 32. If the distance between the virtual training partner 14 and the participant 10 increases, the virtual training partner audio source 34 may in turn decrease the amplitude of the footsteps. Similarly, the virtual training partner audio source 34 may be configured to vary the frequency of the footsteps depending on whether the virtual training partner 14 is increasing or decreasing his/her pace at any given time. Similar changes in amplitude and frequency can be carried out with respect to other types of training as will be appreciated.

Those having ordinary skill in the art will appreciate that the personal training device 20 as represented in FIG. 3 may be carried out primarily via software executed by a conventional microprocessor. Those having ordinary skill in the art of microprocessor programming will be able to program a device to operate in accordance with the functions described herein without undue effort or experimentation. Accordingly, details regarding such programming are omitted for sake of brevity. In another embodiment, the personal training device 20 may be implemented easily primarily via hardware or a combination of hardware and software as will be readily appreciated.

Figure 4:
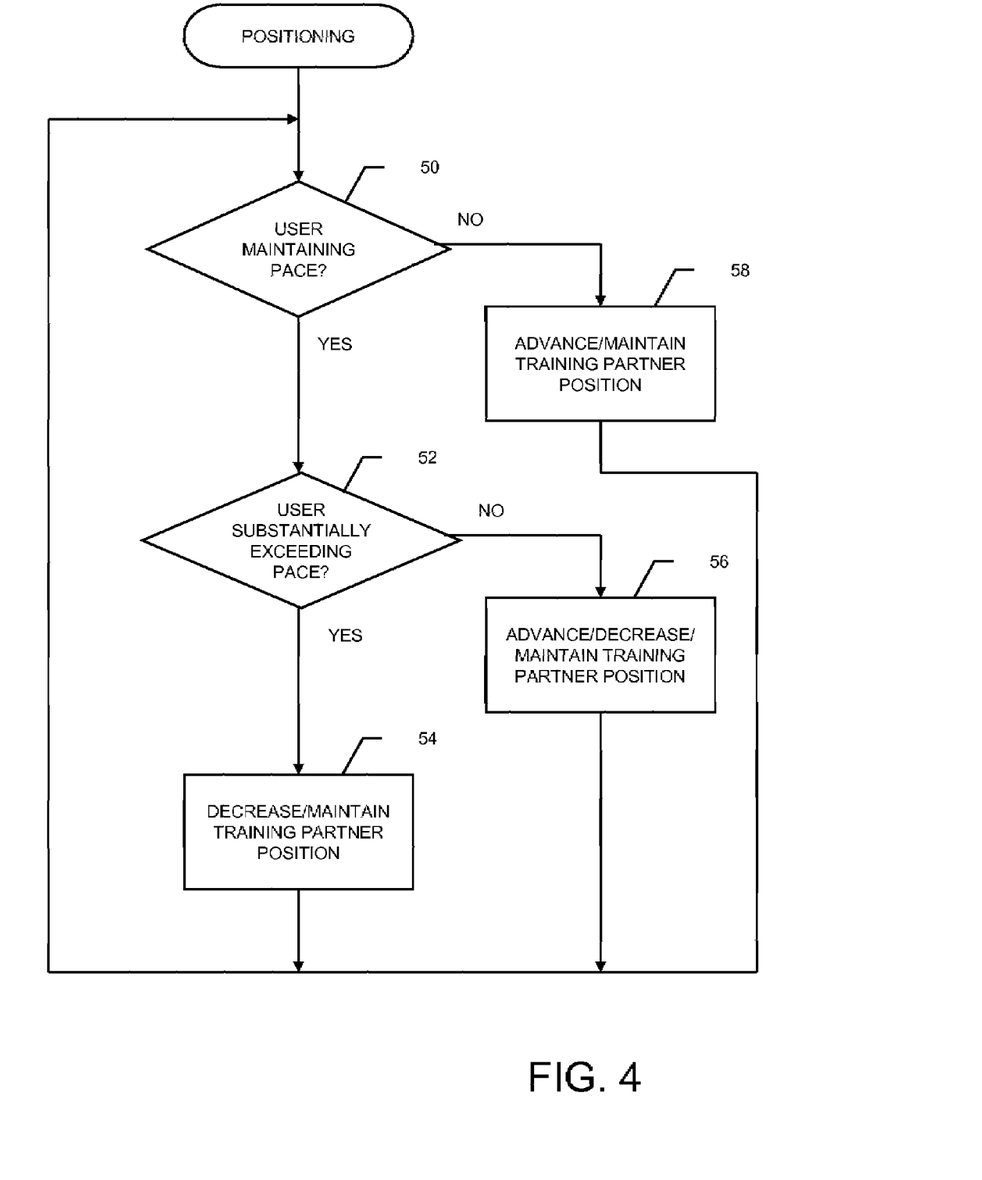
FIG. 4 is a flowchart suitable for programming a personal training device to carry out the functions described herein in accordance with an embodiment of the present invention.

Turning to FIG. 4, the operation process of the personal training device 20 in accordance with an exemplary embodiment is shown. Generally speaking, the personal training device 20 preferably is predominantly configured to advance the position of the virtual training partner 14 within the audio field in the case where the participant 10 falls behind a desired pace, to maintain the position of the virtual training partner 14 when the participant 10 maintains the desired pace, and to decrease the position of the virtual training partner 14 when the participant 10 exceeds the desired pace. As is discussed below with respect to FIG. 4, however, the personal training device 20 may be configured to deviate occasionally from such predominant response in order to introduce some variation, and thereby provide an even more lifelike experience to the participant 10.

More particularly, at the beginning of a training session the training partner positioner 30 preferably is configured to position the virtual training partner 14 adjacent the participant 10, such as to the immediate left or right of the participant 10. Such positioning is, of course, indicative of starting at the same location. Beginning at step 50, the pace comparator 28 determines if the participant 10 is maintaining a desired pace by comparing the pace of the participant 10 as determined by the participant pace calculator 22 with the comparison pace data from comparison data block 24. If yes, the personal training device 20 proceeds to step 52 whereat it is determined if the participant 10 is substantially exceeding the desired pace based on the output of the pace comparator 28. Whether the participant 10 is exceeding the desired pace substantially can be based on a predefined criteria. For example, the participant 10 is considered to substantially exceed the desired pace if the pace of the participant 10 is at least X % (e.g., 10%) greater than the desired pace as represented by the comparison data block 24.

If yes in step 52, the participant 10 is considered to be significantly exceeding his or her desired pace, and the virtual training partner positioner 30 decreases or maintains the position of the virtual training partner 14 relative to the participant 10 as represented in step 54. For example, the virtual training partner positioner 30 may decrease the position of the virtual training partner 14 relative to the participant 10 to reflect the participant 10 closing a gap between the participant 10 and the virtual training partner 14 in the case where the participant 10 is trailing; or to reflect the participant 10 increasing the gap between the virtual training partner 14 and the participant 10 in the case where the participant 10 is leading the virtual training partner 14. In another instance, the virtual training partner positioner 30 may maintain the position of the virtual training partner 14 relative to the participant 10 so as to have the virtual training partner 14 effectively keep pace with the participant 10 despite the participant 10 exceeding the desired pace. In this manner, the personal training device 10 can prompt the participant 10 to improve beyond the desired goals.

Whether the virtual training partner positioner 30 decreases or maintains the position of the virtual training partner 14 relative to the participant 10 can be configured to be effected somewhat randomly so as to provide the participant 10 with varying reactions by the virtual training partner 14. Preferably, the virtual training partner positioner 30 tends to decrease the position of the virtual training partner 14 more often that maintaining the position in step 54 in order to enable the participant 10 to enjoy a feeling of success as a result of substantially exceeding the desired pace. However, the extent to which the virtual training partner positioner 30 decreases versus maintains the position in step 54 may be configured as a function of the particular training level selected by the participant 10 as will be appreciated. Also, the rate at which the position is changed may be altered somewhat randomly in order to better reflect what would occur in real life training. Following step 54, the process then returns to step 50.

If no in step 52, the participant 10 is not considered to be substantially exceeding his or her desired pace, but rather is essentially maintaining the desired pace. Consequently, the virtual training partner positioner 30 may advance, decrease and/or maintain the position of the virtual training partner 14 relative to the participant 10 as represented in step 56. Since the participant 10 is essentially maintaining the desired pace, the position of the virtual training partner 14 may be somewhat randomly varied to provide the participant 10 with varying stimulii. By advancing the position of the virtual training partner 14, the participant 10 is motivated to increase his/her pace. By decreasing the position of the virtual training partner 14, the participant 10 achieves the pleasurable sensation of gaining on and/or moving beyond the virtual training partner 14. By maintaining the position of the virtual training partner 14, the participant 10 receives satisfaction of keeping up with the desired pace.

Since the participant 10 is at least maintaining the desired pace as determined in step 52, the virtual training partner positioner 30 preferably is configured to give preference to maintaining the position of the virtual training partner 14 relative to the participant 10. Again, however, the extent to which the virtual training partner positioner 30 advances, decreases or maintains the position in step 56 may be configured as a function of the particular training level selected by the participant 10 as will be appreciated. Following step 56, the process returns to step 50.

If the participant 10 is not maintaining the desired pace as determined in step 50, the process proceeds to step 58. In step 58, the virtual training partner positioner 30 preferably advances or maintains the position of the virtual training partner 14 relative to the participant 10. Since the participant 10 is failing to maintain the desired pace, the virtual training partner positioner 30 is configured so as to typically advance the position of the virtual training partner 14. By advancing the position of the virtual training partner 14 relative to the participant 10, the participant 10 is motivated to increase his/her pace so as to either catch up to, remain with, or further advance in position relative to the virtual training partner 14. By sometimes maintaining the position of the virtual training partner 14 occasionally in step 58, the participant 10 is in essence provided with a time in which to recover prior to being prompted to increase his or her pace. Again, the extent to which the virtual training partner positioner 30 advances or maintains the position in step 58 may be configured as a function of the particular training level selected by the participant 10 as will be appreciated. Following step 56, the process returns to step 50.

Figure 5:
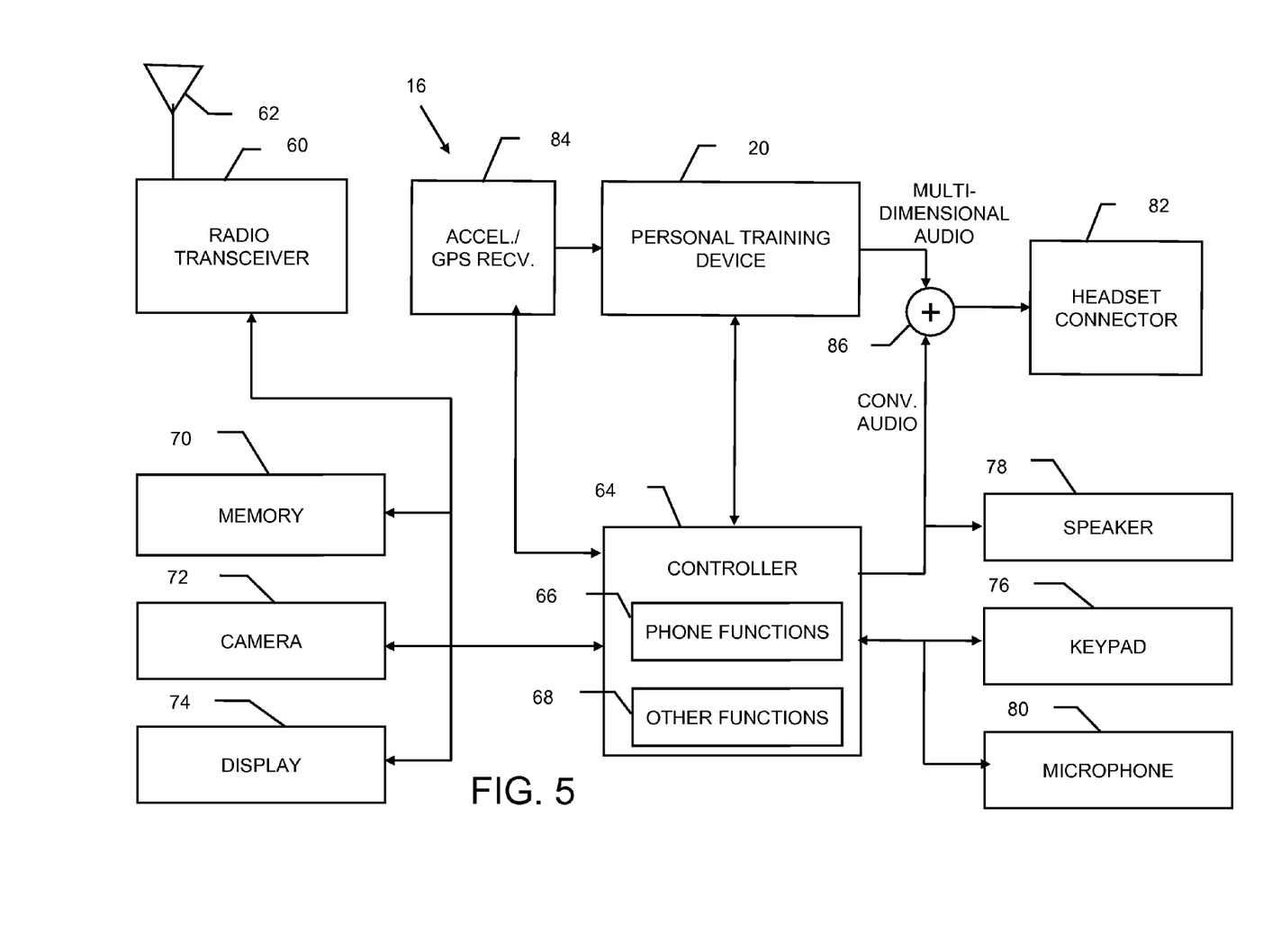
FIG. 5 is a block diagram of the mobile phone of FIG. 2 in accordance with an embodiment of the present invention.

Referring briefly to FIG. 5, the mobile phone 16 of FIG. 2 is shown incorporating the personal training device 20 in accordance with an embodiment of the present invention. The phone 16 includes the conventional features of a radio transceiver 60 and antenna 62 for carrying out mobile communications with a corresponding cell tower, satellite, etc. A controller 64 provides control of the various functions within the phone 16, including conventional phone functions 66 and auxiliary functions 68 (e.g., media player, data organization, etc.). In addition, the controller 64 may be programmed to carry out the above-described processing associated with performing as a personal training device. In FIG. 5 the personal training device 20 is shown as a separate block within the phone 16. However, it will be appreciated that the personal training device functionality may be incorporated within the controller 64 or provided via a separate circuit without departing from the scope of the invention.

The phone 16 further includes memory 70 for storing data for conventional phone operation, data storage and manipulation, etc. In addition, the memory 70 may serve to store the above-described program for carrying out the personal training functionality of the invention, including storing the virtual training partner audio provided to the spatial audio processor 32 as described above. Alternatively, the personal training device 20 may include its own memory for such functions. The phone 16 may further include a camera 72 for performing camera functions, and a display 74 for displaying information such as call status, and user interface menus for enabling a user to enter information such as the afore-described lap times, desired pace, selected training levels, etc., associated with the comparison data block 24.

The phone 16 may additionally include a conventional keypad 76, again for enabling a user to enter information and control the various functions described above, such as selecting that the phone 16 operate in the personal training device mode. The phone 16 further includes a conventional speaker 78 and microphone 80 for permitting a user to carry out conventional mobile communications.

Additionally, the phone 16 includes a headset connector 82 for permitting a multi-channel (e.g., stereophonic) headset such as headset 12 to be connected to the phone 16 for reproducing conventional audio as well as multi-dimensional audio from the personal training device function described herein. The embodiment of the phone 16 as shown in FIG. 2 represents the headset 12 as being a wired headset coupled to the headset connector 82. However, it will be appreciated that the headset connector 82 may also be a wireless headset connector such as a Bluetooth transceiver for connecting to a Bluetooth-compatible headset 12. Alternatively, the headset connector 82 may be some other type of connector (e.g., infrared-based) for connecting wirelessly to a compatible headset 12.

As is shown in FIG. 5, the phone 16 or other device incorporating the personal training device 20 in accordance with the invention may include an accelerometer and/or GPS receiver 84. In this particular embodiment, the participant 10 carries the mobile phone 16 on his or her person during the training session. Consequently, the accelerometer and/or GPS receiver 84 provides an output signal indicative of the movement or pace of the participant 10. The output signal is provided to the personal training device 20 as described above in relation to FIG. 3. The personal training device 20 in turn provides the multi-dimensional audio signal to the headset connector 82 in order that the multi-dimensional audio signal is reproduced via the headset 12 as described above.

In the particular embodiment shown in FIG. 5, the multi-dimensional audio signal output by the personal training device 20 may be combined via an adder 86 with any conventional audio (e.g., mobile communication audio). As a result, the participant 10 may engage in a phone conversation, listen to music, etc., at the same time as participating in a training session.

Based on the above, it will be appreciated that the personal training device of the present invention can improve the training experience for a participant. Specifically, the personal training device can make training sessions more effective and more interesting by incorporating the above-discussed spatial audio techniques.

Still further, the personal training device 20 of the present invention may enable a user to share his or her experiences with others. For example, using the radio transceiver 60, Bluetooth transceiver, or other interface included in the mobile phone 16 or other device, pace times, training levels, etc. of the participant 10 and/or virtual training partners 14 may be uploaded to a network or other device to be shared with others. Alternatively, pace times, training levels, etc., from others may be downloaded from a network or other device for use by the participant 10.

The term "electronic device" as referred to herein includes portable radio communication equipment, and includes all equipment such as mobile phones, pagers, communicators, e.g., electronic organizers, personal digital assistants (PDAs), smartphones or the like.

Although the invention has been shown and described with respect to certain preferred embodiments, it is obvious that equivalents and modifications will occur to others skilled in the art upon the reading and understanding of the specification. For example, the personal training device 20 can be configured to include multiple virtual training partners 14 within the audio field. Each of the virtual training partners may be generated and controlled similar to as described above. Preferably, each of the virtual training partners has their own particular characteristics with respect to the participant 10. In this manner, the participant 10 will perceive the session as training with a group of individualized virtual training partners.

In another embodiment, the radio transceiver 60, a GPS transceiver, a Bluetooth transceiver, or other interface included in the mobile phone 16 or other device may be configured to track a signal provided by a similar device carried by real-life participants training with the participant 10. Position information obtained from other participants is provided to the multi-dimensional spatial audio processor 32 together with appropriate audio. As a result, the participant 10 will also be able to listen to a sound representation of nearby real-life participants.

The present invention includes all such equivalents and modifications, and is limited only by the scope of the following claims.

The invention claimed is:

1. A personal training device for a participant of pace-based physical training, comprising:
    an input for receiving an input signal indicative of a pace of the participant;
    a comparator coupled to the input for comparing the pace of the participant to a predefined criteria;
    a training partner positioner for generating a position of a virtual training partner relative to the participant based on an output of the comparator, wherein the position of the virtual training partner is varied in at least two dimensions relative to the participant; a training partner audio source for providing audio representative of sounds from the virtual training partner;
    a spatial audio processor for producing a multi-dimensional audio signal comprising the audio from the audio source, the multi-dimensional audio signal providing the audio at a spatial location represented by the position generated by the training partner positioner; and
    a global positioning system (GPS) receiver for providing the input signal.

2. The personal training device of claim 1, wherein the training partner positioner adjusts the position of the virtual training partner as a function of whether or not the partner is maintaining a predetermined pace.

3. The personal training device of claim 2, wherein the predetermined pace is based on a training level preselected from among a plurality of different training levels.

4. The personal training device of claim 3, wherein the plurality of training levels each include a predetermined pace which varies as a function of time.

5. The personal training device of claim 2, wherein the predetermined pace is based on a preselected lap time or preselected pace.

6. The personal training partner of claim 2, wherein the training partner positioner tends to advance the position of the virtual training partner relative to the particpant when the runner fails to maintain the predetermined pace, and tends to decrease the position of the virtual training partner relative to the participant when the particpant exceeds the predetermined pace.

7. The personal training device of claim 1, wherein the training partner positioner includes a pseudo-random component for varying the position of the virtual training partner.

8. The personal training device of claim 1, wherein the audio provided by the training partner audio source includes the sound of footsteps of the virtual training partner.

9. The personal training device of claim 8, wherein the training partner audio source varies the frequency of the footsteps as a function of a change in position of the virtual training partner.

10. The personal training device of claim 8, wherein the training partner audio source varies the amplitude of the footsteps as a function of the position of the virtual training partner.

11. The personal training device of claim 1, wherein the audio provided by the training partner audio source includes the sound of cycling.

12. The personal training device of claim 1, wherein the audio provided by the training partner audio source includes voice sounds of the virtual training partner.

13. The personal training device of claim 1, wherein the personal training device is comprised within a portable electronic device.

14. The personal training device of claim 13, wherein the portable electronic device is a mobile phone.

15. The personal training device of claim 1, wherein multiple virtual training partners are provided simultaneously.

* * * * *